US012629496B2

(12) United States Patent
Ohnishi et al.

(10) Patent No.: US 12,629,496 B2
(45) Date of Patent: May 19, 2026

(54) CONTROL SYSTEM, CONTROL DEVICE, AND CONTROL METHOD

(71) Applicants: KEIO UNIVERSITY, Tokyo (JP); MOTION LIB, INC., Kawasaki (JP); TERUMO KABUSHIKI KAISHA, Tokyo (JP)

(72) Inventors: Kouhei Ohnishi, Kawasaki (JP); Takahiro Mizoguchi, Kawasaki (JP); Kazuhiro Yamada, Kanagawa (JP); Yoshiyuki Habu, Kanagawa (JP); Shin Maki, Kanagawa (JP); Toshihiro Fujii, Kanagawa (JP)

(73) Assignees: Keio University, Tokyo (JP); Motion Lib, Inc., Kawasaki-shi (JP); Terumo Kabushiki Kaisha, Tokyo (JP)

( * ) Notice: Subject to any disclaimer, the term of this patent is extended or adjusted under 35 U.S.C. 154(b) by 80 days.

(21) Appl. No.: 18/705,389

(22) PCT Filed: Oct. 10, 2022

(86) PCT No.: PCT/JP2022/037748
§ 371 (c)(1),
(2) Date: Apr. 26, 2024

(87) PCT Pub. No.: WO2023/074335
PCT Pub. Date: May 4, 2023

(65) Prior Publication Data
US 2025/0010034 A1     Jan. 9, 2025

(30) Foreign Application Priority Data

Oct. 29, 2021    (JP) ................................. 2021-178386

(51) Int. Cl.
*A61M 25/01* (2006.01)
*A61B 18/00* (2006.01)
(Continued)

(52) U.S. Cl.
CPC ..... *A61M 25/0116* (2013.01); *A61B 18/1442* (2013.01); *A61B 34/37* (2016.02);
(Continued)

(58) Field of Classification Search
None
See application file for complete search history.

(56) References Cited

U.S. PATENT DOCUMENTS 6,096,004 A      8/2000 Meglan et al.
2007/0142823 A1*  6/2007 Prisco ................... B25J 9/1638
606/1

(Continued)

FOREIGN PATENT DOCUMENTS

JP        S59115172 A     7/1984
JP        2000042116 A    2/2000
(Continued)

OTHER PUBLICATIONS

English Translation of the Written Opinion issued on Jan. 10, 2023, by the International Searching Authority in corresponding International Patent Application No. PCT/JP2022/037748. (4 pages).
International Search Report (PCT/ISA/210) with English translation and Written Opinion (PCT/ISA/237) mailed on Jan. 10, 2023, by the Japanese Patent Office as the International Searching Authority for International Application No. PCT/JP2022/037748, 9 pages.

*Primary Examiner* — Wade Miles
*Assistant Examiner* — Arslan Azhar
(74) *Attorney, Agent, or Firm* — Buchanan Ingersoll & Rooney PC

(57) ABSTRACT

A control system includes a master device, a slave device, and a control device. Furthermore, the control device includes a friction compensation control unit and a tactile force transmission unit. The friction compensation control unit calculates a force for assisting an operation in the master device with respect to friction generated in the slave device on the basis of a moving average of velocity of a movable portion in the slave device. The tactile force transmission (Continued)

unit assists the operation in the master device with a force calculated by the friction compensation control unit and controls tactile force transmission in the master device and the slave device.

7 Claims, 7 Drawing Sheets

(51) Int. Cl.

| | |
|---|---|
| *A61B 18/14* | (2006.01) |
| *A61B 34/30* | (2016.01) |
| *A61B 34/37* | (2016.01) |
| *B25J 9/16* | (2006.01) |
| *B25J 13/02* | (2006.01) |
| *G05B 15/02* | (2006.01) |

(52) U.S. Cl.
CPC ............. *B25J 9/1641* (2013.01); *B25J 13/02* (2013.01); *G05B 15/02* (2013.01); *A61B 2018/0022* (2013.01); *A61B 2034/301* (2016.02)

(56) References Cited

U.S. PATENT DOCUMENTS

| | | | |
|---|---|---|---|
| 2010/0204713 A1 | 8/2010 | Ruiz | |
| 2017/0303773 A1 | 10/2017 | Su et al. | |
| 2018/0243899 A1* | 8/2018 | Hashimoto | B25J 13/087 |
| 2020/0189091 A1 | 6/2020 | Shimomura et al. | |
| 2020/0214779 A1* | 7/2020 | Masuda | G05B 19/056 |
| 2020/0352665 A1* | 11/2020 | Itotani | B25J 13/085 |
| 2021/0107134 A1 | 4/2021 | Shimono et al. | |
| 2022/0378525 A1* | 12/2022 | Yajima | B25J 13/089 |

FOREIGN PATENT DOCUMENTS

| | | | |
|---|---|---|---|
| JP | 2009525097 A | 7/2009 |
| JP | 2017532143 A | 11/2017 |
| JP | 2018192596 A | 12/2018 |
| JP | 2019155497 A | 9/2019 |
| WO | 2018203365 A1 | 11/2018 |

* cited by examiner

CONTROL SYSTEM, CONTROL DEVICE, AND CONTROL METHOD

TECHNICAL FIELD

The present invention relates to a control system, a control device, and a control method.

BACKGROUND ART

Conventionally, a configuration for compensating frictional force in a master-slave manipulator has been known (see, for example, Patent Literature 1).

CITATION LIST

Patent Literature

Patent Literature 1: JP S59-115172 A

SUMMARY OF INVENTION

Technical Problem

The frictional force acting on the slave device may change on the basis of the state change of a slave device. In a case where compensation is performed so as to simply eliminate the frictional force acting on the slave device, it is difficult for the user to perceive the state change of the slave device through a master device. Also, control to compensate for the frictional force may assist unnecessary movement.

That is, there is room for improvement in the control for friction compensation executed in the master-slave system.

Solution to Problem

A control system according to one aspect of the present invention including

- a master device to which an operation by an operator is input and a slave device that operates in accordance with the operation input to the master device, includes:
- a control amount calculation means that calculates a force for assisting an operation in the master device based on information relating to moving of a movable portion in the slave device; and
- a control means that assists the operation in the master device with the force calculated by the control amount calculation means and control tactile force transmission in the master device and the slave device.

Advantageous Effects of Invention

According to the present invention, it is possible to make control for friction compensation executed in a master-slave system more appropriate.

DESCRIPTION OF EMBODIMENTS

Hereinafter, an embodiment of the present invention will be described with reference to the drawings.

First Embodiment

[Configuration]

Figure 1:
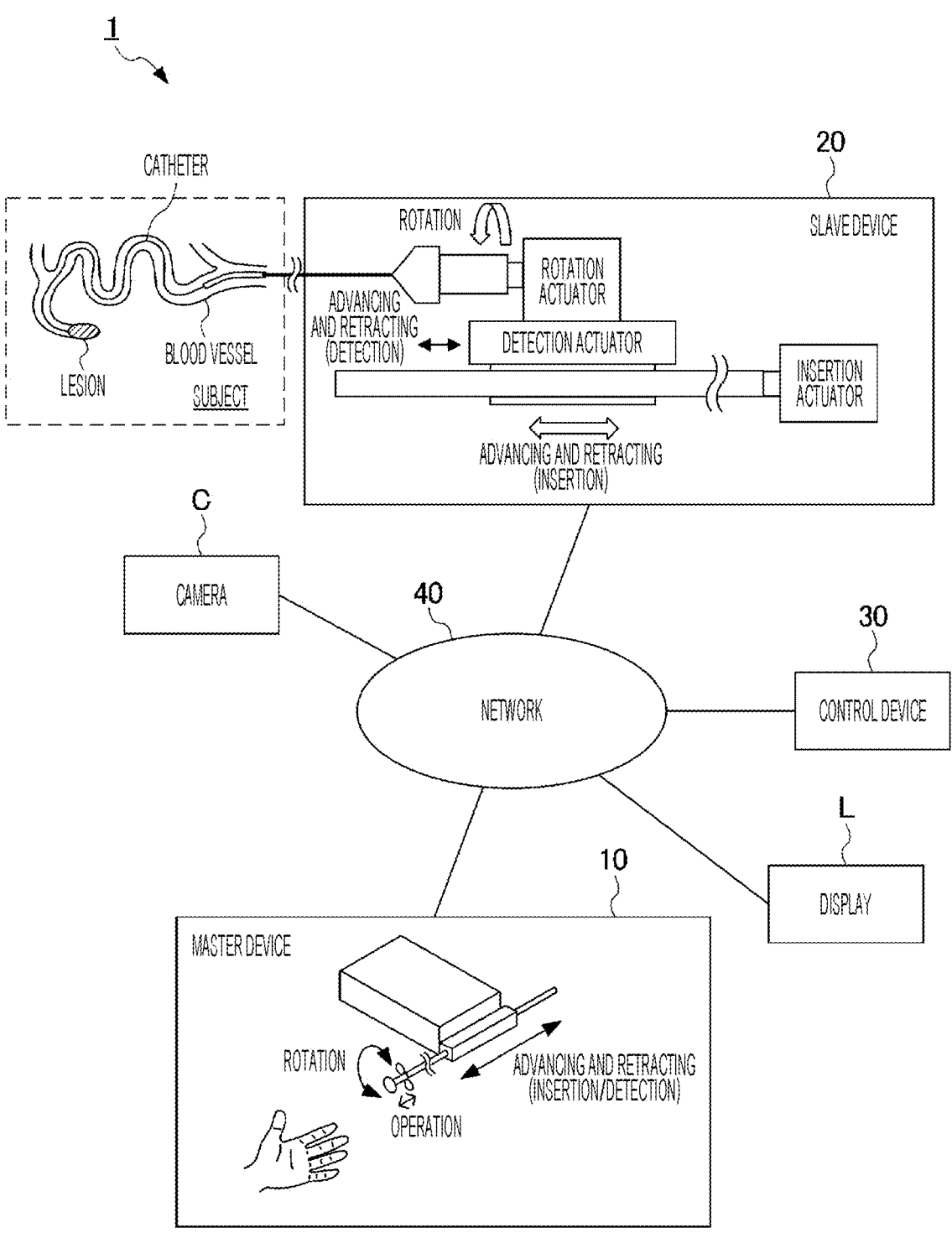
FIG. 1 is a schematic diagram illustrating an overall configuration of a control system 1 according to an embodiment of the present invention.

FIG. 1 is a schematic diagram illustrating an overall configuration of a control system 1 according to an embodiment of the present invention.

As illustrated in FIG. 1, the control system 1 according to the present embodiment is configured as a master-slave system including a master device 10 and a slave device 20 that are mechanically separated. As an example, in the control system 1 in the present embodiment, it is assumed that the master device 10 constitutes a manipulator operated by a user, and the slave device 20 constitutes a catheter system including an end effector to be inserted into a subject.

In FIG. 1, the control system 1 includes the master device 10, the slave device 20, and a control device 30, and the master device 10, the slave device 20, and the control device 30 is configured to perform wired or wireless communication via a network 40. Note that the control system 1 can appropriately include a display L and a plurality of cameras C. As the cameras C, various imaging devices such as a video camera that captures an external appearance of a subject into which the slave device 20 is inserted or an X-ray camera that captures the inside of the subject by X-ray can be used. Furthermore, it is also possible to include a plurality of displays L that displays various images captured by the plurality of cameras C.

The master device 10 receives an operation similar to an operation for a conventional catheter configured mechanically, and detects a position of a movable portion (a movable member of the manipulator, or the like) moved by the input operation. The master device 10 transmits information representing the detected position of the movable portion to the control device 30. Furthermore, the master device 10 outputs reaction force by an actuator in response to the input operation in accordance with an instruction from the control device 30.

Specifically, the master device 10 receives an operation of advancing and retracting the catheter (for example, an operation of inserting the catheter into a blood vessel or the like), an operation of axially rotating the catheter (for example, an operation of changing a direction of the end effector, or the like), and an operation of operating the end effector (for example, in a case where the end effector is a balloon, an operation of expanding and contracting the balloon, and in a case where the end effector is a pair of forceps or the like, an operation of opening and closing the pair of forceps, or the like), and applies reaction force to these operations, and transmits, to the control device 30, information representing a position of the movable portion moved by each operation.

The slave device 20 drives an actuator in accordance with an instruction from the control device 30 to perform an operation corresponding to an operation input to the master device 10, and detects a position of a movable portion (a movable element of the actuator, the catheter moved by the actuator, or the like) moved by the operation. When the slave device 20 operates, various types of external force are input to the slave device 20 from an environment. As a result, the position of the movable portion in the slave device 20 indicates a result of the various types of external force acting on an output of the actuator. Then, the slave device 20 transmits information representing the detected position of the movable portion to the control device 30. Here, the various external forces input from the environment to the slave device 20 include a resistance force in the thrust direction received by the catheter from the blood vessel. In a case where the resistance force in the thrust direction in the slave device 20 is great, there is a possibility that it becomes difficult to perceive other external forces input to the catheter (abutment force upon contact with a lesion or an organ, or the like). In the present embodiment, as will be described later, the friction compensation amount calculated from the moving average value of the advancing and retracting velocity of the catheter in the section set in the past is output as the force for assisting the operation of the operator in the master device 10. As a result, it is possible to make it easy to perceive the state change of the slave device 20 while reducing the burden of the user who operates the master device 10, and it is possible to suppress a situation in which a single vibration occurs in the catheter by the force for assisting the operation.

The control device 30 includes, for example, an information processing device such as a personal computer (PC) or a server computer, and controls the master device 10, the slave device 20, the display L, and the cameras C. For example, the control device 30 executes control for acquiring positions of the movable portions of the master device 10 and the slave device 20 (rotation angles of the actuators detected by rotary encoders, advancing and retracting positions of the movable portions detected by linear encoders, or the like), and transmitting tactile force between the master device 10 and the slave device 20.

When operating the master device 10 and the slave device 20 as the master-slave system, the control device 30 in the present embodiment performs coordinate transformation (transformation by a transformation matrix) of parameters (input vectors) of a real space calculated on the basis of information representing the positions of the movable portions (information representing positions of movable elements of the actuators, positions of members moved by the actuators, or the like) into a virtual space in which a position and force can be handled independently. That is, coordinate transformation of the input vectors from the real space of an oblique coordinate system in which a position and force are related to each other to the virtual space of an orthogonal coordinate system in which a position and force are independent from each other is performed. The parameters calculated by the coordinate transformation represent state values of positions and force corresponding to the input vectors in the virtual space. Then, in the virtual space after the coordinate transformation, the control device 30 performs an arithmetic operation to cause the state values of the positions and the force calculated from the input vectors to follow the respective target values of the positions and the force for performing control of the positions and the force (here, tactile force transmission), and performs inverse transformation (transformation by an inverse matrix of the transformation matrix) to return an arithmetic operation result to the real space. Moreover, the control device 30 implements the master-slave system that transmits tactile force between the master device 10 and the slave device 20 by driving each actuator on the basis of the parameters (a current command value and the like) of the real space acquired by the inverse transformation.

The control device 30 in the present embodiment outputs the friction compensation amount calculated from the moving average value of the advancing and retracting velocity of the catheter in the section set in the past as the force for assisting the operation of the operator in the master device 10, when transmitting the tactile force between the master device 10 and the slave device 20.

Note that, since the position and a velocity (or acceleration) or an angle and an angular velocity (or angular acceleration) are parameters that can be replaced by a differential and integral operation, it is possible to appropriately replace them with the velocity, the angular velocity, or the like when processing related to the position or the angle is performed.

Figure 2:
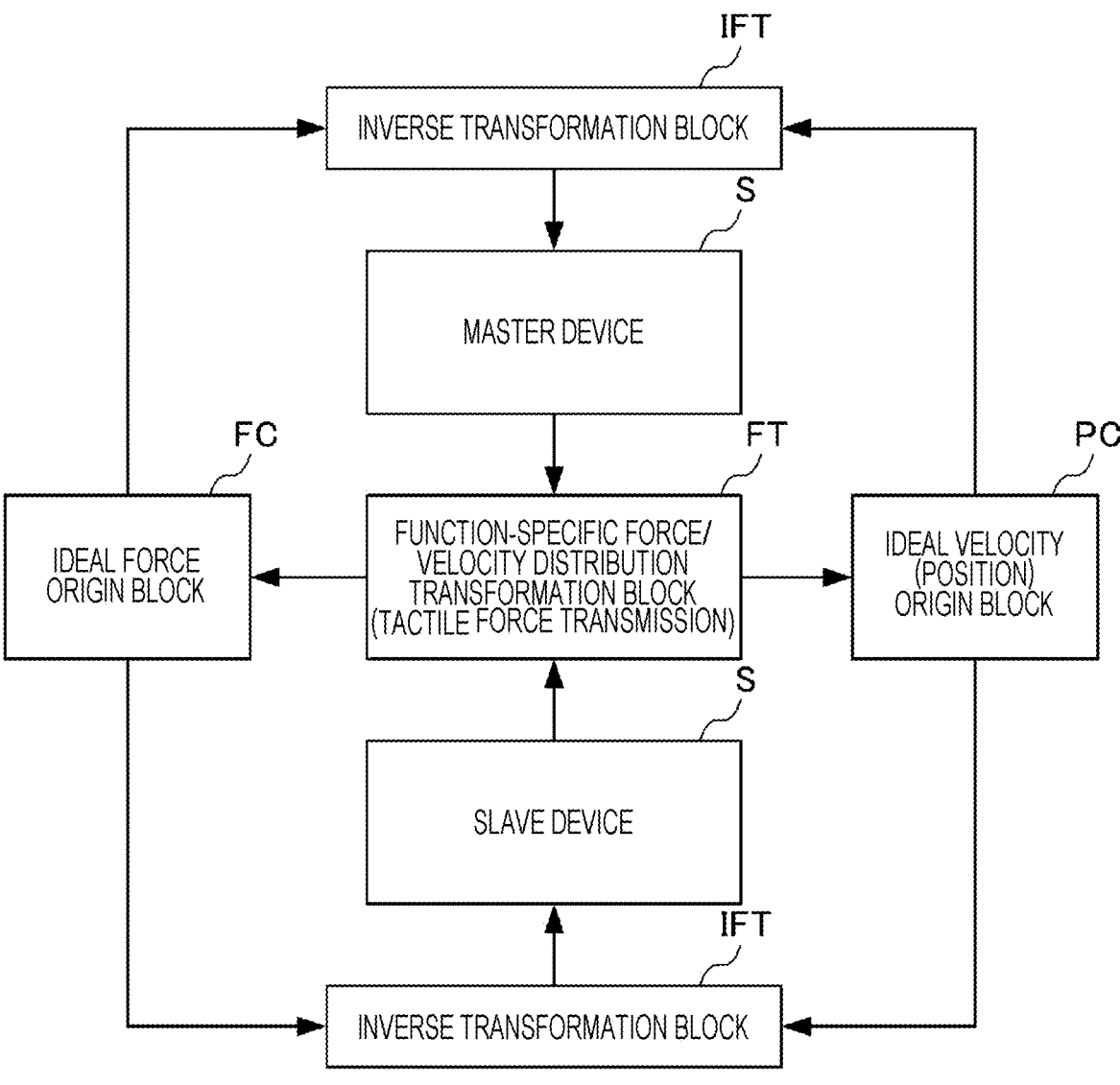
FIG. 2 is a schematic diagram illustrating a basic principle of tactile force transmission control executed by a control device 30.

FIG. 2 is a schematic diagram illustrating a basic principle of tactile force transmission control executed by the control device 30.

The basic principle illustrated in FIG. 2 is to determine an operation of the actuator by performing an arithmetic operation in at least one domain of a velocity or force with information representing a position of the movable portion (current position of the movable portion) as an input.

That is, the basic principle of the present invention is represented as control rules including a control object system S, a function-specific force/velocity distribution transformation block FT, at least one of an ideal force origin block FC or an ideal velocity origin block PC, and an inverse transformation block IFT.

The control object system S is the master device 10 or the slave device 20 including the actuator, and controls the actuator on the basis of the acceleration or the like. Here, as described above, since the acceleration, the velocity, and the position are physical quantities that can be mutually transformed by differentiation and integration, any of the acceleration, the velocity, and the position may be used for the control. Here, it is assumed that the control rules are expressed by mainly using the velocity calculated from the position.

The function-specific force/velocity distribution transformation block FT is a block that defines transformation of control energy in the domains of the velocity and the force, which is set in accordance with a function of the control object system S. Specifically, the function-specific force/velocity distribution transformation block FT defines coordinate transformation whose inputs are a value serving as a reference (reference value) for the function of the control object system S and a current position of the movable portion. The coordinate transformation is generally transformation of an input vector whose elements are a reference value and a current velocity to an output vector including a velocity for calculating a control target value of a velocity, and transformation of an input vector whose elements are a reference value and current force to an output vector including force for calculating a control target value of force.

Specifically, the coordinate transformation in the function-specific force/velocity distribution transformation block FT can be generalized and represented as in the following Expressions (1) and (2).

[Math. 1]

$$\begin{pmatrix} \dot{x}_1 \\ \dot{x}_2 \\ \vdots \\ \dot{x}_{n-1} \\ \dot{x}_n \end{pmatrix} = \begin{pmatrix} h_{1a} & h_{1b} & \cdots & h_{1(m-1)} & h_{1m} \\ h_{2a} & h_{2b} & \cdots & h_{2(m-1)} & h_{2m} \\ \vdots & \vdots & \ddots & \vdots & \vdots \\ h_{(n-1)a} & h_{(n-1)b} & \cdots & h_{(n-1)(m-1)} & h_{(n-1)m} \\ h_{na} & h_{nb} & \cdots & h_{n(m-1)} & h_{nm} \end{pmatrix} \begin{pmatrix} \dot{x}_a \\ \dot{x}_b \\ \vdots \\ \dot{x}_{m-1} \\ \dot{x}_m \end{pmatrix} \quad (1)$$

$$\begin{pmatrix} f_1 \\ f_2 \\ \vdots \\ f_{n-1} \\ f_n \end{pmatrix} = \begin{pmatrix} h_{1a} & h_{1b} & \cdots & h_{1(m-1)} & h_{1m} \\ h_{2a} & h_{2b} & \cdots & h_{2(m-1)} & h_{2m} \\ \vdots & \vdots & \ddots & \vdots & \vdots \\ h_{(n-1)a} & h_{(n-1)b} & \cdots & h_{(n-1)(m-1)} & h_{(n-1)m} \\ h_{na} & h_{nb} & \cdots & h_{n(m-1)} & h_{nm} \end{pmatrix} \begin{pmatrix} f_a \\ f_b \\ \vdots \\ f_{m-1} \\ f_m \end{pmatrix} \quad (2)$$

Note that, in Expression (1), x'$_1$ to x'$_n$ (n is an integer equal to or greater than 1) represent velocity vectors for deriving a state value of a velocity, x'$_a$ to x'$_m$ (m is an integer equal to or greater than 1) represent vectors whose elements are a reference value and a velocity based on an action of the actuator (a velocity of the movable element of the actuator or a velocity of a member moved by the actuator), and h$_{1a}$ to h$_{nm}$ represent elements of a transformation matrix representing the function. Furthermore, in Expression (2), f"$_1$ to f"$_n$ (n is an integer equal to or greater than 1) represent force vectors for deriving a state value of force, and f"$_a$ to f"$_m$ (m is an integer equal to or greater than 1) represent vectors whose elements are a reference value and force based on an action of the actuator (force of the movable element of the actuator or force of a member moved by the actuator).

By setting the coordinate transformation in the function-specific force/velocity distribution transformation block FT in accordance with the function to be implemented, various operations may be implemented and scaling may be performed.

That is, in the basic principle of the present invention, the function-specific force/velocity distribution transformation block FT "transforms" a variable (variable in the real space) of a single actuator to a variable group (variables in the virtual space) of the entire system expressing the function to be implemented, and distributes the control energy to velocity control energy and force control energy. In other words, the basic principle of the present invention transforms a coordinate space in which the velocity and the force are related to each other into a coordinate space in which the velocity and the force are independent from each other, and then performs an arithmetic operation regarding control of the velocity and the force. Thus, as compared with a case where the control is performed by using the variable (variable in the real space) of the single actuator, the velocity control energy and the force control energy may be given independently.

The ideal force origin block FC is a block that performs arithmetic operations in the domain of the force in accordance with coordinate transformation defined by the function-specific force/velocity distribution transformation block FT. The ideal force origin block FC sets a target value related to force in performing an arithmetic operation based on the coordinate transformation defined by the function-specific force/velocity distribution transformation block FT. The target value is set as a fixed value or a variable value in accordance with a function to be implemented. For example, in a case where the function to be implemented is similar to a function indicated by a reference value, the target value can be set to zero, and in a case where scaling is performed, a value obtained by expanding or reducing information indicating the function to be implemented can be set.

The ideal velocity origin block PC is a block that performs an arithmetic operation in the domain of the velocity in accordance with coordinate transformation defined by the function-specific force/velocity distribution transformation block FT. The ideal velocity origin block PC sets a target value related to a velocity in performing an arithmetic operation based on the coordinate transformation defined by the function-specific force/velocity distribution transformation block FT. The target value is set as a fixed value or a variable value in accordance with a function to be implemented. For example, in a case where the function to be implemented is similar to a function indicated by a reference value, the target value can be set to zero, and in a case where scaling is performed, a value obtained by expanding or reducing information indicating the function to be implemented can be set.

The inverse transformation block IFT is a block that transforms values in the domains of the velocity and the force to values in a domain of an input to the control object system S (for example, voltage values, current values, or the like).

According to such a basic principle, when information regarding a position in the actuator of the control object system S is input to the function-specific force/velocity distribution transformation block FT, the function-specific force/velocity distribution transformation block FT uses information regarding a velocity and force obtained on the basis of the information regarding the position to apply the control rules corresponding to a function in each of the domains of the position and the force. Then, an arithmetic operation of force corresponding to the function is performed in the ideal force origin block FC, an arithmetic operation of a velocity corresponding to the function is performed in the ideal velocity origin block PC, and control energy is allocated to each of the force and the velocity.

Arithmetic operation results in the ideal force origin block FC and the ideal velocity origin block PC are information indicating control targets of the control object system S. These arithmetic operation results are used as input values of the actuator in the inverse transformation block IFT and input to the control object system S.

As a result, the actuator of the control object system S executes an operation in accordance with the function defined by the function-specific force/velocity distribution transformation block FT, and the operation of the device that is the object is implemented.

Furthermore, in a case where a tactile force transmission function involving scaling (amplification of force or a position) is implemented, the coordinate transformation in the function-specific force/velocity distribution transformation block FT in FIG. 2 is represented as the following Expressions (3) and (4).

[Math. 2]

$$\begin{pmatrix} \dot{x}_p \\ \dot{x}_f \end{pmatrix} = \begin{pmatrix} 1 & -\alpha \\ 1 & \beta \end{pmatrix} \begin{pmatrix} \dot{x}_m \\ \dot{x}_s \end{pmatrix} \quad (3)$$

$$\begin{pmatrix} f_p \\ f_f \end{pmatrix} = \begin{pmatrix} 1 & -\alpha \\ 1 & \beta \end{pmatrix} \begin{pmatrix} f_m \\ f_s \end{pmatrix} \quad (4)$$

Note that, in Expression (3), x'$_p$ is a velocity for deriving a state value of a velocity, and x'$_f$ is a velocity related to a state value of force. Furthermore, $x'_m$ is a velocity of a reference value (input from the master device 10) (a differential value of a current position of the master device 10), and x's is a current velocity of the slave device 20 (a differential value of the current position). Furthermore, in Expression (4), $f_p$ is force related to a state value of a velocity, and $f_f$ is force for deriving a state value of force. Furthermore, $f_m$ is force of a reference value (input from the master device 10), and $f_s$ is current force of the slave device 20.

In the case of the coordinate transformation indicated in Expressions (3) and (4), a position of the slave device 20 is multiplied by α (α is a positive number) and transmitted to the master device 10, and force of the slave device 20 is multiplied by β (β is a positive number) and transmitted to the master device 10. In the case of amplifying only the force transmitted from the slave device 20 to the master device 10, it is sufficient that α=1 holds and a value of β is set in accordance with the objective.

[Hardware Configuration]

Next, a hardware configuration of a control system in the control system 1 will be described.

Figure 3:
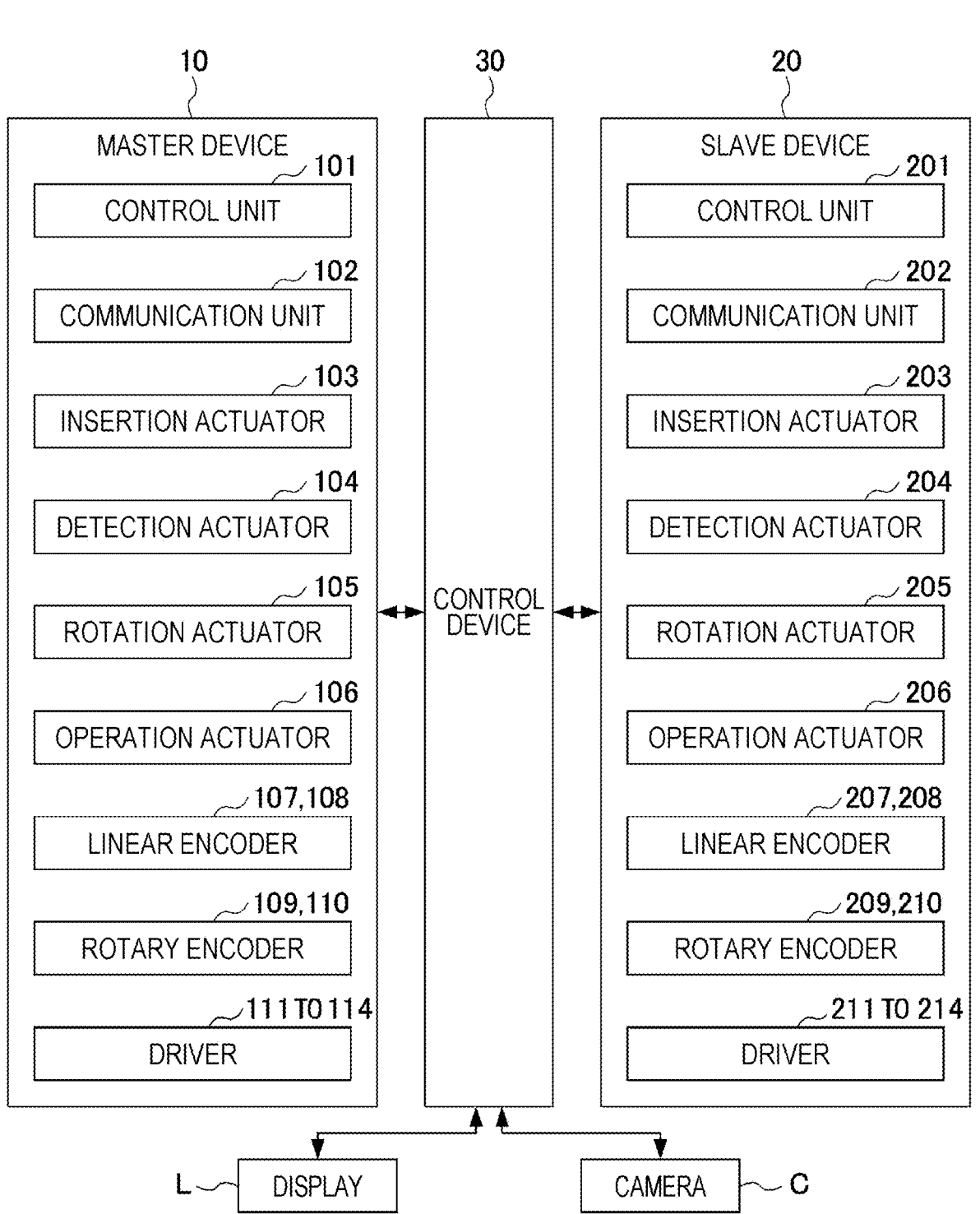
FIG. 3 is a block diagram illustrating a hardware configuration of a control system in the control system 1.

FIG. 3 is a block diagram illustrating the hardware configuration of the control system in the control system 1.

As illustrated in FIG. 3, the control system 1 includes, as the hardware configuration of the control system, the control device 30 including the information processing device such as a PC or a server computer, a control unit 101, a communication unit 102, an insertion actuator 103, a detection actuator 104, a rotation actuator 105, an operation actuator 106, linear encoders 107 and 108, rotary encoders 109 and 110, and drivers 111 to 114 of the master device 10, a control unit 201, a communication unit 202, an insertion actuator 203, a detection actuator 204, a rotation actuator 205, an operation actuator 206, linear encoders 207 and 208, rotary encoders 209 and 210, and drivers 211 to 214 of the slave device 20, the display L, and the cameras C.

The control unit 101 of the master device 10 includes a microcomputer including a processor, a memory, and the like, and controls an operation of the master device 10. For example, the control unit 101 controls driving of the insertion actuator 103, the detection actuator 104, the rotation actuator 105, and the operation actuator 106 of the master device 10 in accordance with control parameters transmitted from the control device 30.

The communication unit 102 controls communication performed by the master device 10 with another device via the network 40.

The insertion actuator 103 includes, for example, a linear motion motor, and applies reaction force to an operation of advancing and retracting the catheter for inserting the catheter into a blood vessel, which is input to the master device 10 by an operator, in accordance with an instruction from the control unit 101.

The detection actuator 104 includes, for example, a voice coil motor, and applies reaction force to an operation of advancing and retracting the catheter for treatment near a lesion, which is input to the master device 10 by an operator, in accordance with an instruction from the control unit 101.

In the present embodiment, the insertion actuator 103 has a longer stroke than the detection actuator 104, while the detection actuator 104 can control a position and force with higher accuracy than the insertion actuator 103.

The rotation actuator 105 includes, for example, a rotary motor, and applies reaction force to an operation of rotating the master device 10 about a rotation axis along an advancing and retracting direction by an operator, in accordance with an instruction from the control unit 101.

The operation actuator 106 includes, for example, a rotary motor, and applies reaction force to an operation input to a lever (grip portion) or the like for operating the end effector by an operator, in accordance with an instruction from the control unit 101.

The linear encoder 107 detects a position (advancing and retracting position on a translation axis) of a movable element of the insertion actuator 103.

The linear encoder 108 detects a position (advancing and retracting position on a translation axis) of a movable element of the detection actuator 104.

The rotary encoder 109 detects a position (rotation angle) of a movable element of the rotation actuator 105.

The rotary encoder 110 detects a position (rotation angle) of a movable element of the operation actuator 106.

The driver 111 outputs a drive current to the insertion actuator 103 in accordance with an instruction from the control unit 101.

The driver 112 outputs a drive current to the detection actuator 104 in accordance with an instruction from the control unit 101.

The driver 113 outputs a drive current to the rotation actuator 105 in accordance with an instruction from the control unit 101.

The driver 114 outputs a drive current to the operation actuator 106 in accordance with an instruction from the control unit 101.

The control unit 201 of the slave device 20 includes a microcomputer including a processor, a memory, and the like, and controls an operation of the slave device 20. For example, the control unit 201 controls driving of the insertion actuator 203, the detection actuator 204, the rotation actuator 205, and the operation actuator 206 of the slave device 20 in accordance with control parameters transmitted from the control device 30.

The communication unit 202 controls communication performed by the slave device 20 with another device via the network 40.

The insertion actuator 203 includes, for example, a linear motion motor, and advances and retracts the catheter of the slave device 20 in accordance with an operation of advancing and retracting the catheter for inserting the catheter into a blood vessel, which is input to the master device 10 by an operator, in accordance with an instruction from the control unit 201.

The detection actuator 204 includes, for example, a voice coil motor, and advances and retracts the catheter of the slave device 20 in accordance with an operation of advancing and retracting the catheter for treatment near a lesion, which is input to the master device 10 by an operator, in accordance with an instruction from the control unit 201.

In the present embodiment, the insertion actuator 203 has a longer stroke than the detection actuator 204, while the detection actuator 204 can control a position and force with higher accuracy than the insertion actuator 203.

The rotation actuator 205 includes, for example, a rotary motor, and rotates the catheter of the slave device 20 about a rotation axis along an advancing and retracting direction in accordance with an operation input to the master device 10 by an operator, in accordance with an instruction from the control unit 201.

The operation actuator 206 includes, for example, a rotary motor, and operates (performs an expansion/contraction operation, an opening/closing operation, and the like on) the end effector in accordance with an operation input to the master device 10 by an operator, in accordance with an instruction from the control unit 201.

The linear encoder 207 detects a position (advancing and retracting position on a translation axis) of a movable element of the insertion actuator 203.

The linear encoder 208 detects a position (advancing and retracting position on a translation axis) of a movable element of the detection actuator 204.

The rotary encoder 209 detects a position (rotation angle) of a movable element of the rotation actuator 205.

The rotary encoder 210 detects a position (rotation angle) of a movable element of the operation actuator 206.

The driver 211 outputs a drive current to the insertion actuator 203 in accordance with an instruction from the control unit 201.

The driver 212 outputs a drive current to the detection actuator 204 in accordance with an instruction from the control unit 201.

The driver 213 outputs a drive current to the rotation actuator 205 in accordance with an instruction from the control unit 201.

The driver 214 outputs a drive current to the operation actuator 206 in accordance with an instruction from the control unit 201.

The display L is installed at a place where an operator of the master device 10 can visually recognize a screen, and displays an image (such as a visible light image or an X-ray image of a subject captured by the camera C) instructed to be displayed by the control device 30.

The camera C is installed at a place where the slave device 20 can capture a subject into which the catheter is inserted, captures an image (such as a visible light image or an X-ray image) of the subject, and transmits the captured image to the control device 30.

Figure 4:
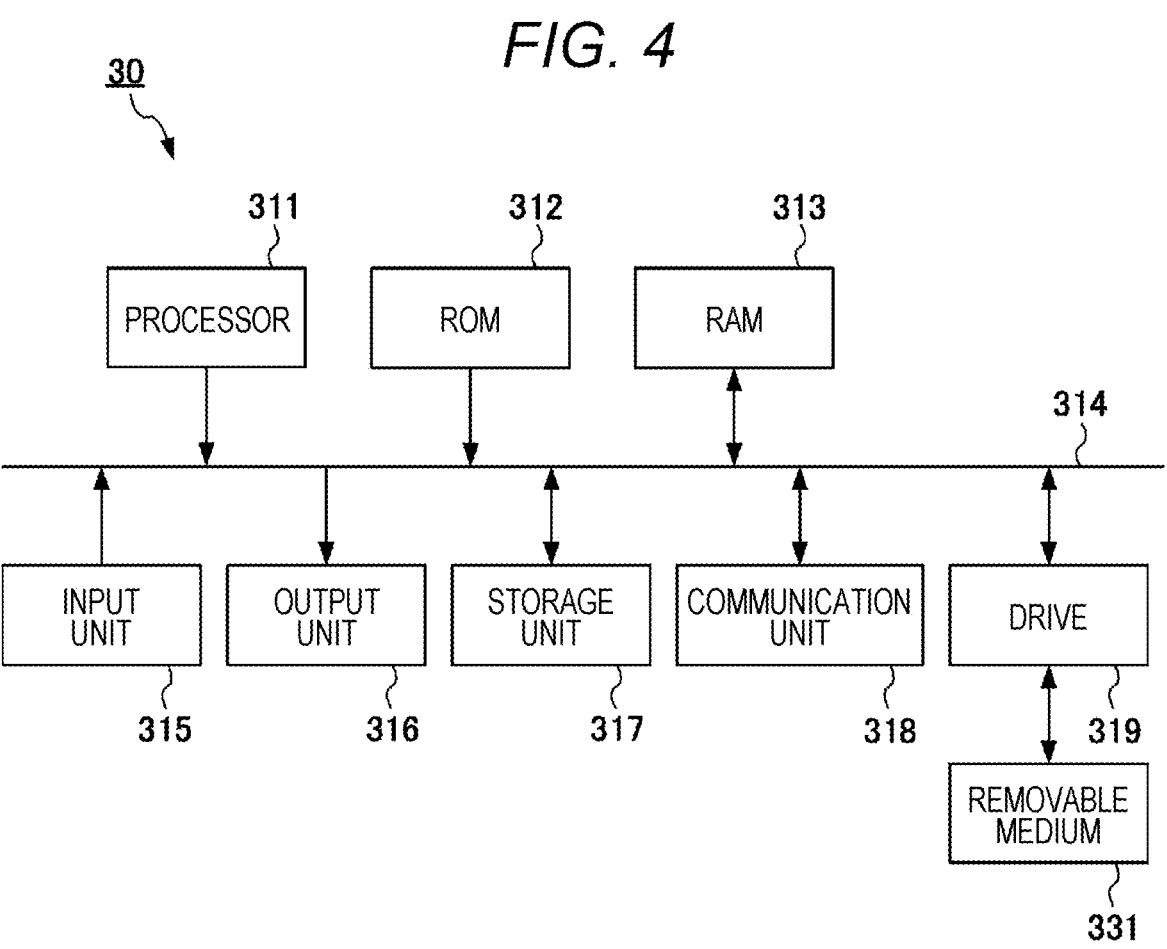
FIG. 4 is a schematic diagram illustrating a hardware configuration of an information processing device constituting the control device 30.

FIG. 4 is a schematic diagram illustrating a hardware configuration of the information processing device constituting the control device 30.

As illustrated in FIG. 4, the control device 30 includes a processor 311, a read only memory (ROM) 312, a random access memory (RAM) 313, a bus 314, an input unit 315, an output unit 316, a storage unit 317, a communication unit 318, and a drive 319.

The processor 311 executes various types of processing in accordance with a program recorded in the ROM 312 or a program loaded from the storage unit 317 to the RAM 313.

The RAM 313 appropriately stores data and the like necessary for the processor 311 to execute various types of processing.

The processor 311, the ROM 312, and the RAM 313 are mutually connected via the bus 314. The input unit 315, the output unit 316, the storage unit 317, the communication unit 318, and the drive 319 are connected to the bus 314.

The input unit 315 includes various buttons and the like, and inputs various types of information in accordance with an instruction operation.

The output unit 316 includes a display, a speaker, and the like, and outputs an image and sound.

Note that, in a case where the control device 30 is configured as a smartphone or a tablet terminal, the input unit 315 and the display of the output unit 316 may be arranged in an overlapping manner to configure a touch panel.

The storage unit 317 includes a hard disk, a dynamic random access memory (DRAM), or the like, and stores various types of data managed by each server.

The communication unit 318 controls communication performed by the control device 30 with another device via the network.

A removable medium 331 including a magnetic disk, an optical disk, a magneto-optical disk, a semiconductor memory, or the like is appropriately mounted on the drive 319. A program read from the removable medium 331 by the drive 319 is installed in the storage unit 317 as necessary.

[Functional Configuration]

Next, a functional configuration of the control system 1 will be described.

Figure 5:
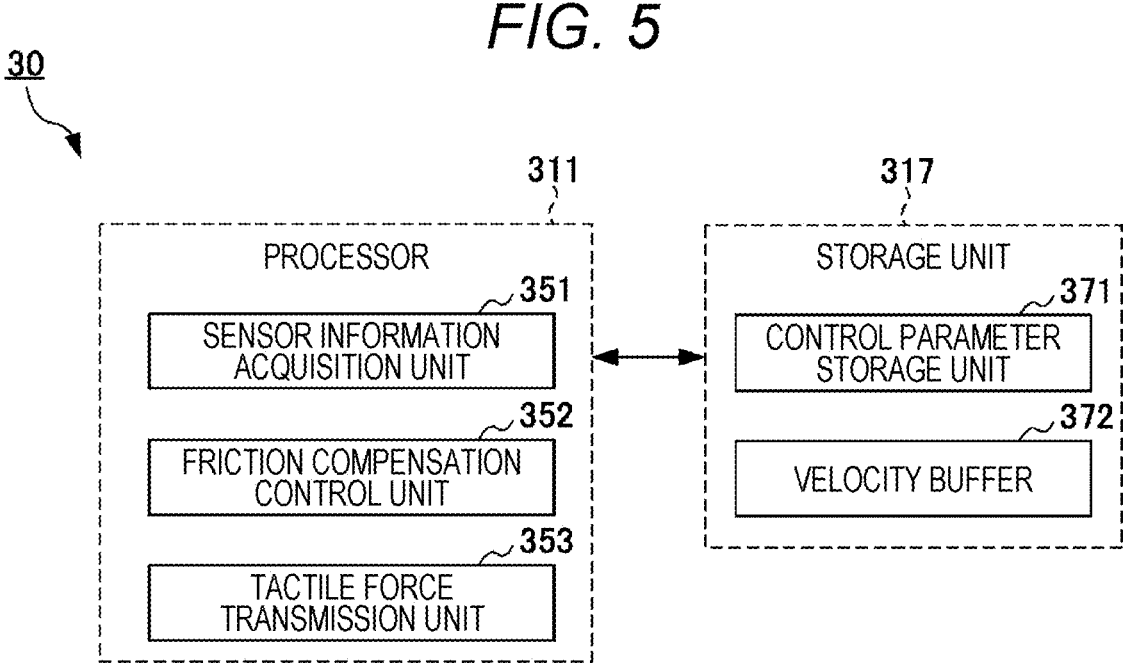
FIG. 5 is a block diagram illustrating a functional configuration of the control system 1.

FIG. 5 is a block diagram illustrating the functional configuration of the control system 1.

As illustrated in FIG. 5, in the control system 1, the control device 30 executes various types of processing, whereby the sensor information acquisition unit 351, the friction compensation control unit 352, and the tactile force transmission unit 353 function in the processor 311. In addition, a control parameter storage unit 371 and a velocity buffer 372 are formed in the storage unit 317.

The control parameter storage unit 371 stores, in time series, control parameters acquired in control in which the control device 30 transmits tactile force between the master device 10 and the slave device 20. In the present embodiment, information stored as the control parameters can be various parameters acquired by the tactile force transmission control, and can include various types of information capable of reproducing the tactile force transmission control. For example, sensor information acquired in the master device 10 and the slave device 20, a state value obtained by coordinate transformation of the sensor information, a current command value to each actuator, various setting values set in the control device 30 for the tactile force transmission control, and the like can be stored as the control parameters.

The velocity buffer 372 stores data of the advancing and retracting velocity of the catheter calculated by the friction compensation control unit 352 in the section defined in the past (for example, past five seconds). The data of the advancing and retracting velocity of the catheter stored in the velocity buffer 372 is sequentially updated to the latest data every time the friction compensation control unit 352 newly calculates the advancing and retracting velocity of the catheter.

The sensor information acquisition unit 351 acquires information (sensor information) detected by various sensors installed in the master device 10 and the slave device 20. For example, the sensor information acquisition unit 351 acquires information indicating the positions (the advancing and retracting positions or the rotation angles) of the movable elements of the actuators detected by the linear encoders 107, 108, 207, and 208 and the rotary encoders 109, 110, 209, and 210. Furthermore, the sensor information acquisition unit 351 stores the acquired sensor information in the control parameter storage unit 371 as time-series data.

The friction compensation control unit 352 calculates the current advancing and retracting velocity (current value) of the catheter in the slave device 20 on the basis of the sensor information acquired by the sensor information acquisition unit 351. In addition, the friction compensation control unit 352 stores the calculated current advancing and retracting velocity (current value) of the catheter in the velocity buffer 372 in association with time. Then, the friction compensation control unit 352 calculates an average value (that is, the moving average value) of the advancing and retracting velocity of the catheter in the section defined in the past, and multiplies the calculated moving average value by the friction compensation coefficient set for friction compensation to calculate a friction compensation amount (force for assisting the operation) output to the user in the master device 10. Here, a simple moving average value is used as the moving average value.

The tactile force transmission unit 353 controls tactile force transmission in the master device 10 and the slave device 20 in accordance with the control algorithm illustrated in FIG. 2. For example, the tactile force transmission unit 353 executes control to transmit tactile force between the actuators for corresponding operations of the master device 10 and the slave device 20 in tactile force transmission processing. In a case where the external force input to the slave device 20 is enlarged and transmitted to the master device 10, the position (velocity) or the force detected by the slave device 20 can be enlarged and transmitted to the master device 10.

Furthermore, the tactile force transmission unit 353 performs control to compensate for the frictional force input to the slave device 20 with the friction compensation amount calculated by the friction compensation control unit 352. That is, the tactile force control unit 353 outputs the friction compensation amount calculated from the moving average value of the advancing and retracting velocity of the catheter in the section set in the past as the force for assisting the operation of the operator in the master device 10.

Here, since the catheter has elasticity, for example, when an external force is input to the slave device 20 due to a transient noise such as unexpected contact by the operator, the elastic force of the catheter acts on the input, and the catheter is pushed back.

At this time, in a case where friction compensation is simply performed, the operation of the catheter is amplified, and a single vibration occurs.

In addition, even in a case where no external force is input to the slave device 20, a minute velocity may be detected in the advancing and retracting direction by the sensor, and in a case where simple friction compensation is performed, the minute velocity is subjected to the friction compensation. Then, the operation in the advancing and retracting direction is assisted, and a single vibration is generated.

On the other hand, by outputting the friction compensation amount obtained by multiplying the average value (that is, the moving average value) of the advancing and retracting velocity of the catheter in the section defined in the past by the friction compensation coefficient as the force for assisting the operation of the user in the master device 10, the assisting force is not applied to the velocity component with which the catheter vibrates, and the assisting force is applied to the velocity component in which the catheter moves in one direction.

As a result, it is possible to make it easy to perceive the state change of the slave device 20 while reducing the burden of the user who operates the master device 10, and it is possible to suppress a situation in which a single vibration occurs in the catheter by the force for assisting the operation.

Therefore, the control for friction compensation performed in the master-slave system can be made more appropriate.

[Operation]

Next, an operation of the control system 1 will be described.

[Tactile Force Transmission Processing]

Figure 6:
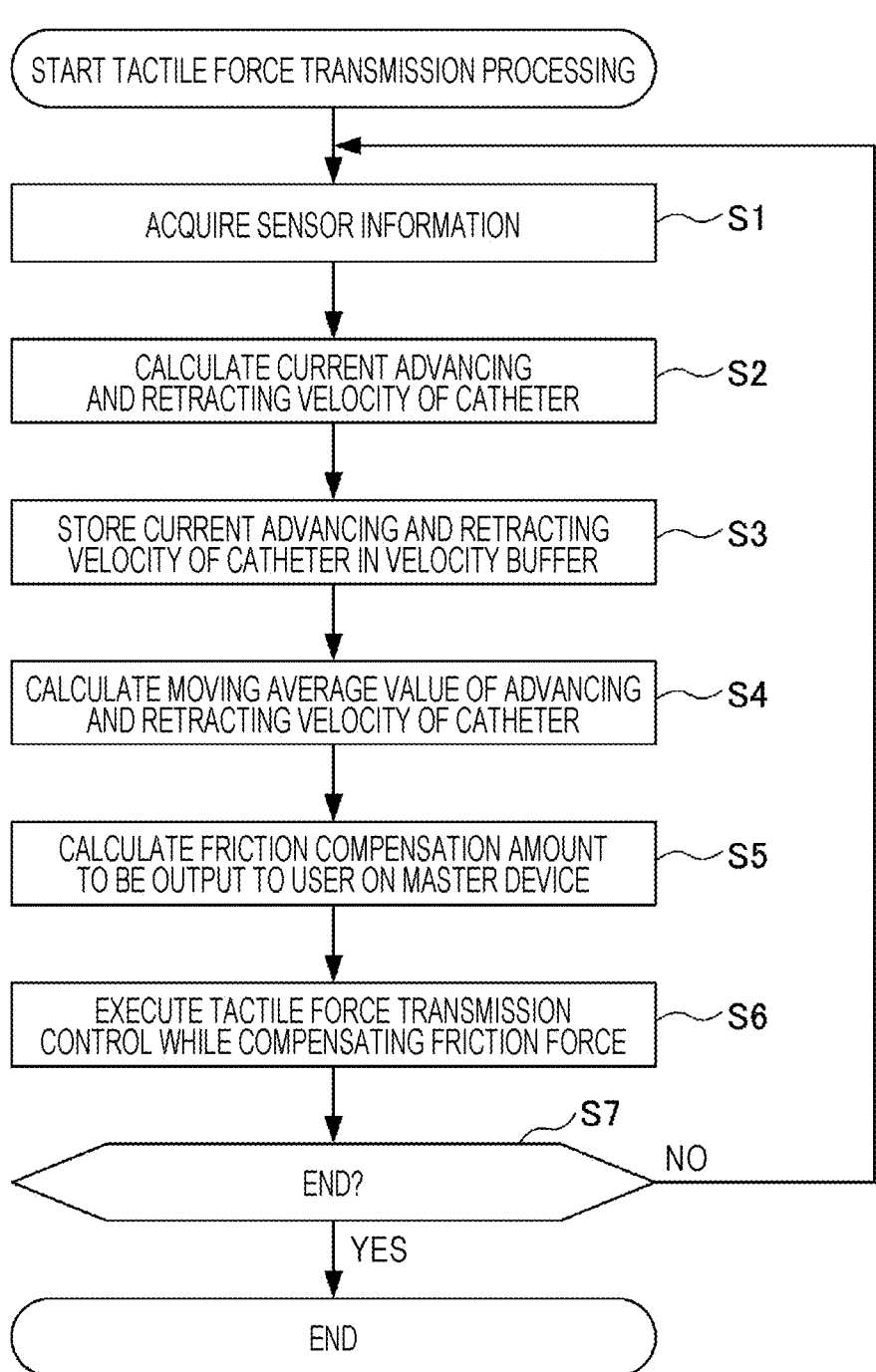
FIG. 6 is a flowchart for describing a flow of tactile force transmission processing executed by the control device 30.

FIG. 6 is a flowchart for describing a flow of the tactile force transmission processing executed by the control device 30.

The tactile force transmission processing is started in response to an instruction to execute the tactile force transmission processing via the input unit 315 or the communication unit 318. In the present embodiment, in a case where the tactile force transmission processing is started, it is assumed that the processing is started in a state where the distal end of the catheter is inserted into a subject manually by an operator assisting an operation of the slave device 20 or by a remote operation from the master device 10.

In step S1, the positional information acquisition unit 351 acquires information (sensor information) detected by various sensors installed in the master device 10 and the slave device 20. The sensor information acquired in step S1 is stored in the control parameter storage unit 371 as time-series data.

In step S2, the friction compensation control unit 352 calculates the current advancing and retracting velocity (current value) of the catheter in the slave device 20 on the basis of the sensor information acquired by the sensor information acquisition unit 351.

In step S3, the friction compensation control unit 352 stores the calculated current advancing and retracting velocity (current value) of the catheter in the velocity buffer 372 in association with time.

In step S4, the friction compensation control unit 352, the friction compensation control unit 352 calculates the average value (that is, the moving average value) of the advancing and retracting velocity of the catheter in the section defined in the past.

In step S5, the friction compensation control unit 352 calculates the friction compensation amount to be output to the user in the master device 10 by multiplying the calculated moving average value by the friction compensation coefficient set for the friction compensation.

In step S6, the tactile force transmission unit 353 controls tactile force transmission in the master device 10 and the slave device 20 while compensating for the frictional force input to the slave device 20 with the friction compensation amount calculated by the friction compensation control unit 352.

In step S7, the tactile force transmission unit 353 determines whether or not end of the tactile force transmission processing is instructed.

In a case where the end of the tactile force transmission processing is not instructed, determination in step S7 is NO, and the processing proceeds to step S1.

In a case where the end of the tactile force transmission processing is instructed, determination in step S7 is YES, and the tactile force transmission processing ends.

[Verification of Effect]

Figure 7:
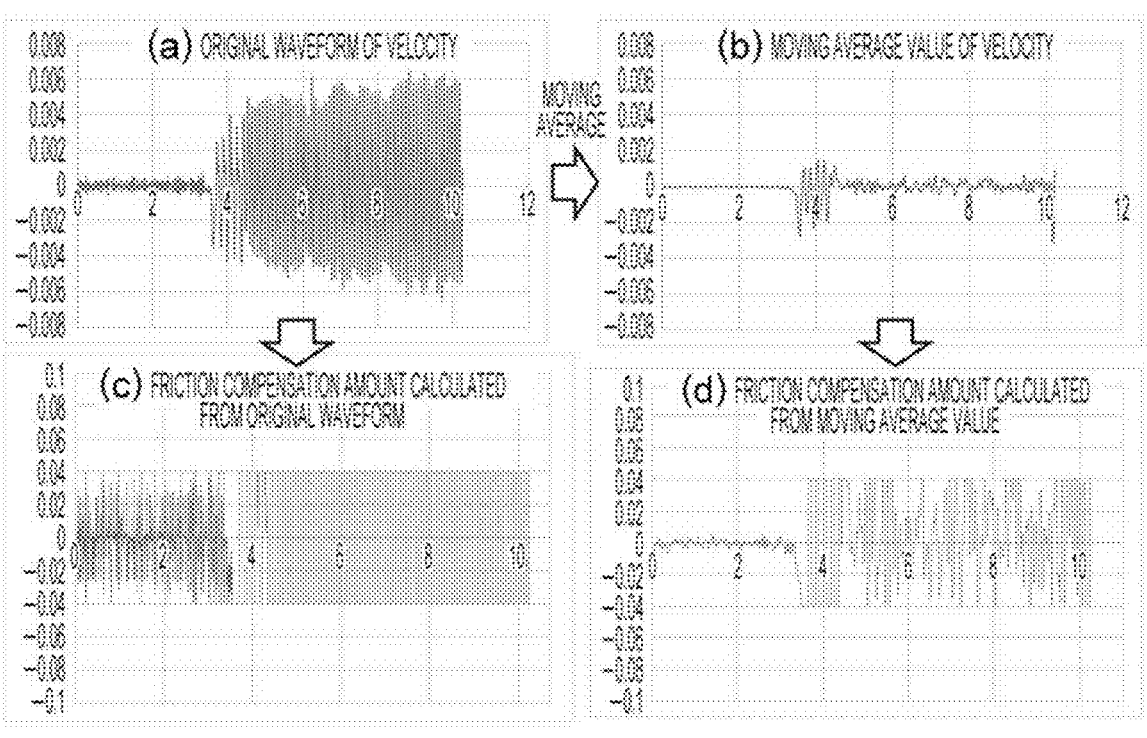
FIG. 7 is a schematic view illustrating a relationship between a velocity of a catheter and a friction compensation amount.

FIG. 7 is a schematic view illustrating a relationship between a velocity of a catheter and a friction compensation amount.

FIG. 7 illustrates (a) an original waveform of the velocity in a case where catheter vibration is generated, (b) a moving average value of the velocity in a case where catheter vibration is generated (a waveform obtained by canceling 10 [Hz] or more of the original waveform), (c) a friction compensation amount calculated from the original waveform of the velocity, and (d) a friction compensation amount calculated from the moving average value of the velocity. The waveform illustrated in FIG. 7 indicates a temporal change of the normalized velocity or friction compensation amount.

As illustrated in FIG. 7 (*c*), when the friction compensation amount is simply calculated from the original waveform of the velocity in a case where vibration of the catheter is generated, an action of maintaining or increasing the vibration of the catheter acts, and the vibration is maintained for a long time.

On the other hand, as illustrated in FIG. 7 (d), when the friction compensation amount is calculated from the moving average value of the velocity in a case where vibration of the catheter is generated, it is found that the action of maintaining or increasing the vibration of the catheter is reduced.

As described above, the control system 1 according to the present embodiment outputs the friction compensation amount obtained by multiplying the average value (that is, the moving average value) of the advancing and retracting velocity of the catheter in the section defined in the past by the friction compensation coefficient as the force for assisting the operation of the user in the master device 10. As a result, the assisting force is not applied to the velocity component in which the catheter vibrates, and the assisting force is applied to the velocity component in which the catheter moves in one direction.

As a result, in the case of compensating for the frictional force input to the slave device 20, it is possible to make it easy to perceive the state change of the slave device 20 while reducing the burden of the user who operates the master device 10, and it is possible to suppress a situation in which a single vibration occurs in the catheter by the force for assisting the operation.

Therefore, the control for friction compensation performed in the master-slave system can be made more appropriate.

Second Embodiment

In the first embodiment, the friction compensation amount obtained by multiplying the average value (that is, the moving average value) of the advancing and retracting velocity of the catheter in the section defined in the past by the friction compensation coefficient is output as the force for assisting the operation of the user in the master device 10.

On the other hand, in the present embodiment, when calculating the average value (that is, the moving average value) of the catheter advancing and retracting velocity in the section defined in the past, the moving average value of the advancing and retracting velocity having the forgetting characteristic is calculated by multiplying the advancing and retracting velocity at a time closer to the current time by the forgetting coefficient with a higher weight being set.

As a result, when a change occurs in the state of the external force in the slave device 20, the change can be more quickly reflected to perform friction compensation.

The control system 1 in the present embodiment is different from the control system 1 in the first embodiment in the configuration of the friction compensation control unit 352.

Therefore, the configuration of the friction compensation control unit 352, which is a different portion, will be mainly described below.

The friction compensation control unit 352 calculates the current advancing and retracting velocity (current value) of the catheter in the slave device 20 on the basis of the sensor information acquired by the sensor information acquisition unit 351. In addition, the friction compensation control unit 352 stores the calculated current advancing and retracting velocity (current value) of the catheter in the velocity buffer 372 in association with time. Then, the friction compensation control unit 352 calculates a weighted average value (hereinafter referred to as "moving average value with forgetting coefficient") based on the forgetting coefficient with respect to the advancing and retracting velocity of the catheter in the section defined in the past, and multiplies the calculated moving average value with the forgetting coefficient by the friction compensation coefficient set for friction compensation to calculate a friction compensation amount (force for assisting the operation) output to the user in the master device 10.

The moving average value of the advancing and retracting velocity of the catheter in the section defined in the past in the first embodiment is expressed by, for example, the following Expression (5).

On the other hand, in the present embodiment, when the moving average value with the forgetting coefficient is calculated with respect to the advancing and retracting velocity of the catheter in the section defined in the past, it can be calculated by the following Expression (6).
[Math. 3]

$$\frac{1}{m}\sum_{k=0}^{m}x[n-k] \tag{5}$$

$$\sum_{k=0}^{\infty}x[n-k]e^{-\frac{k}{T}} \tag{6}$$

Note that, in Expressions (5) and (6), m represents the number of data in the moving average section, n represents a data number of a current value, k represents the number of data going back from the current value, T represents a time constant, and $\exp(-k/T)$ represents a forgetting coefficient. The time constant T can be determined as an appropriate value with reference to an experimental value, a value obtained by simulation, or the like on the basis of, for example, the behavior of the control system 1 in a case where the friction compensation amount is calculated using the simple moving average.

The calculation of the moving average value with the forgetting coefficient shown in Expression (6) corresponds to calculation of applying the primary IIR low-pass filter to the waveform of the advancing and retracting velocity of the catheter.

Figure 8:
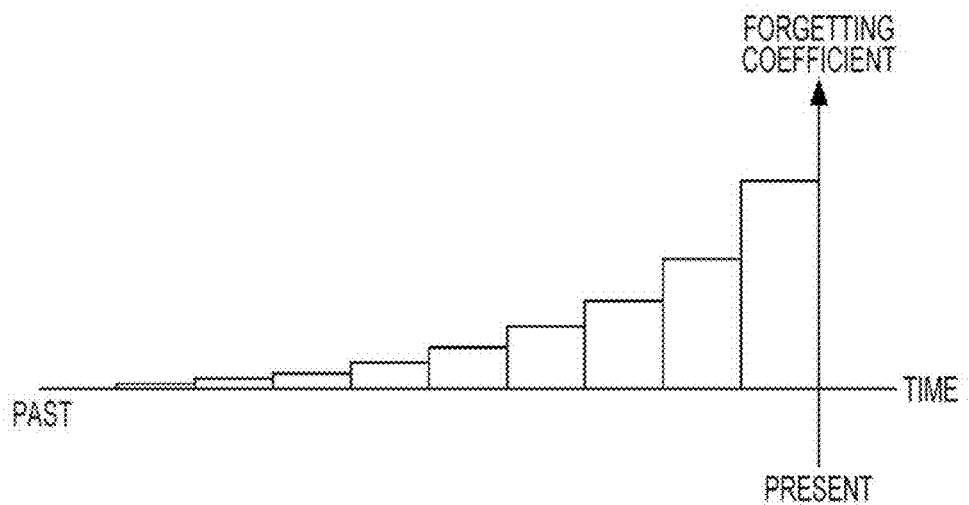
FIG. 8 is a schematic diagram illustrating a forgetting coefficient of a moving average value with a forgetting coefficient represented by Expression (6).

FIG. 8 is a schematic diagram illustrating a forgetting coefficient of a moving average value with a forgetting coefficient represented by Expression (6).

As illustrated in FIG. 8, the forgetting coefficient used when the moving average value with the forgetting coefficient is calculated has a larger value at a time closer to the current time and a smaller value at a past time farther from the current time.

The tactile force transmission unit 353 performs control to compensate for the frictional force input to the slave device 20 using the friction compensation amount calculated in this manner as in the first embodiment.

As described above, the control system 1 in the present embodiment calculates the moving average value with the forgetting coefficient of the advancing and retracting velocity of the catheter in the section defined in the past, and multiplies the moving average value with the forgetting coefficient by the friction compensation coefficient set for friction compensation to calculate a friction compensation amount output to the user in the master device 10. Then, the friction compensation amount calculated in this manner is output as a force for assisting the user's operation on the master device 10. As a result, the assisting force is not applied to the velocity component in which the catheter vibrates, and the assisting force is applied to the velocity component in which the catheter moves in one direction. Furthermore, due to the characteristics of the moving average value with the forgetting coefficient, the moving average value is calculated with a smaller weight in the past data of the advancing and retracting velocity of the catheter, so that the effect of compensating for the frictional force corresponding to the current advancing and retracting velocity of the catheter is enhanced.

As a result, in the case of compensating for the frictional force input to the slave device 20, it is possible to make it easy to perceive the state change of the slave device 20 while reducing the burden of the user who operates the master device 10, and it is possible to suppress a situation in which a single vibration occurs in the catheter by the force for assisting the operation. In addition, even in a case where an external force is input to the slave device 20 due to a transient noise, the force for assisting the advancing and retracting of the catheter caused by the external force and the elastic force of the catheter are balanced, so that it is possible to suppress the catheter from being temporarily stopped in the middle of vibration, and the like. That is, since the friction compensation amount is not constant (constantly changes due to the action of the forgetting coefficient) by multiplying the moving average value by the forgetting coefficient, in the moving average section, a stationary state is less likely to occur due to the balance between the steady force generated by the input of the external force based on the transient noise and the elastic force of the catheter at the specific position. In addition, since the vibration component of the friction compensation amount calculated by multiplying the moving average value by the forgetting coefficient is reduced by the effect of the moving average, it is possible to further suppress the occurrence of vibration in the catheter.

Therefore, the control for friction compensation performed in the master-slave system can be made more appropriate.

First Modification

In the above-described embodiment, it has been described that the force for friction compensation in the master device 10 (force for assisting operation) is output with respect to the advancing and retracting velocity of the catheter.

On the other hand, it is possible to output the force for friction compensation in consideration of an element other than the advancing and retracting velocity of the catheter.

For example, since the angle at which the slave device 20 is installed constantly causes the influence of gravity on the advancing and retracting movements, a force for assisting the operation in the master device 10 with respect to gravity (force for inclination compensation) can be output.

In this case, for example, the friction compensation control unit 352 calculates a component of gravity acting in the advancing and retracting direction of the catheter on the basis of the inclination angle at which the slave device 20 is installed, and calculates a force for inclination compensation corresponding to the calculated component of gravity (such as multiplying the component of gravity by a coefficient), and the tactile force transmission unit 353 can assist the force for inclination compensation in the master device 10. At this time, in the advancing and retracting direction of the catheter, a negative assist (that is, the force by which the component of gravity interferes with the action of moving the catheter) can be output in the same direction as the component of gravity, and a positive assist (a force that suppresses an action of the gravity component inhibiting the movement of the catheter) can be output in the opposite direction to the component of gravity.

As a result, it is possible to compensate for the influence of gravity input to the slave device 20, reduce the burden on the user operating the master device 10, and make it easy to perceive the state change (the magnitude of the actual load, or the like) of the slave device 20.

Therefore, the control for friction compensation performed in the master-slave system can be made more appropriate.

Second Modification

In the embodiment described above, the configuration has been described as an example in which the actuator operates after the catheter is inserted until the catheter reaches a lesion, but the present invention is not limited thereto. For example, the catheter may be manually inserted to near the lesion, and force may be fed back from the slave device 20 to the master device 10 in a specific section near the lesion. In this case, the operator manually inserts the catheter of the slave device 20 to the vicinity of the lesion, and in the vicinity of the lesion, tactile force transmission is performed while friction-compensating the force input to the slave device 20 with the friction compensation amount being set on the basis of the moving average value of the advancing and retracting velocity of the catheter.

Figure 9:
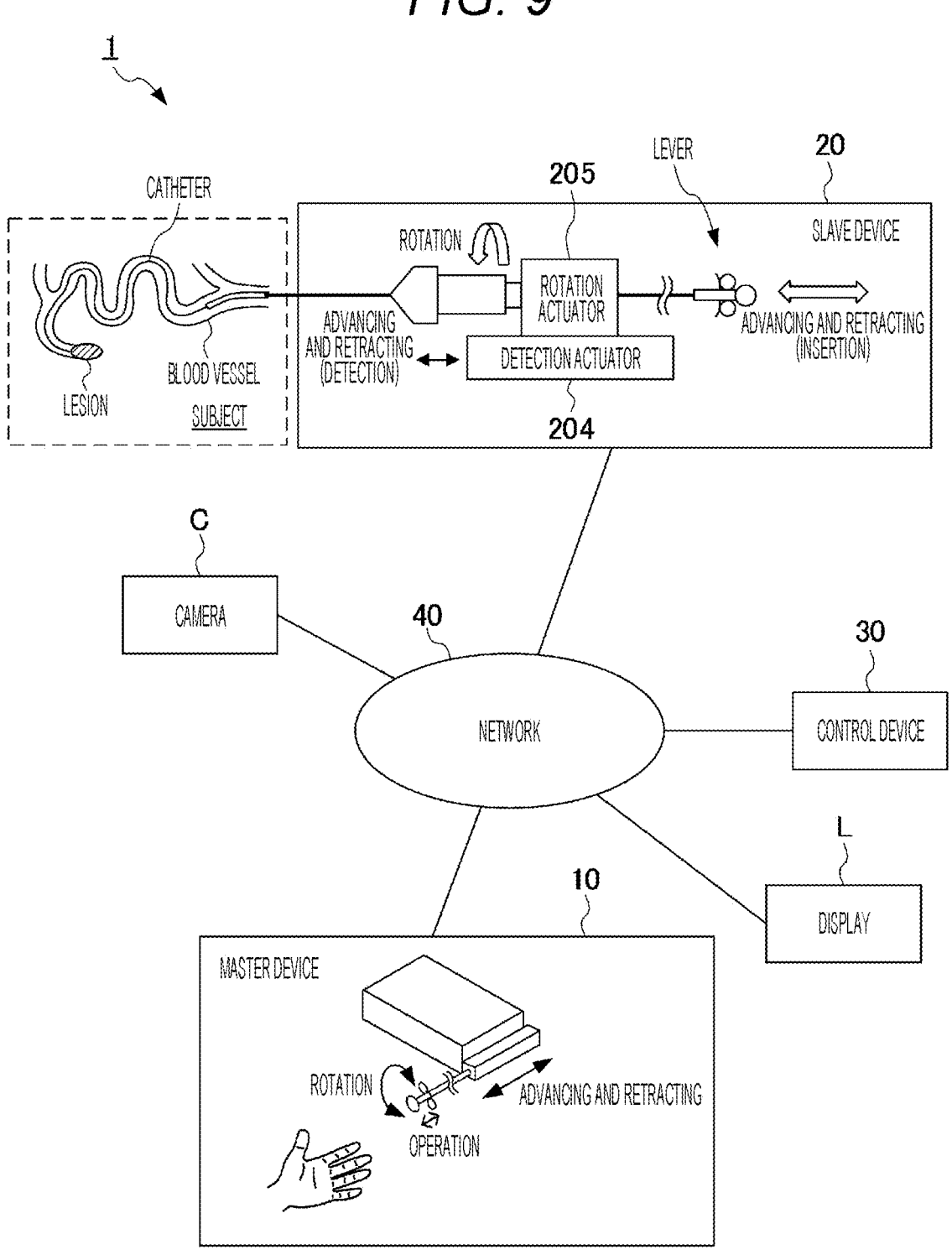
FIG. 9 is a schematic diagram illustrating a configuration of the control system 1 that performs feedback of force after an operator manually inserts a catheter of the slave device 20.

FIG. 9 is a schematic diagram illustrating a configuration of the control system 1 that performs feedback of force after an operator manually inserts the catheter of the slave device 20.

As illustrated in FIG. 9, in the control system 1 of the present modification, a lever (grip portion) or the like for operation is installed in the catheter of the slave device 20, and a manual operation by an operator is possible.

Furthermore, the control system 1 of the present modification includes only the detection actuators 104 and 204 and does not include the insertion actuators 103 and 203 among the linear motion actuators included in the control system 1 of the first embodiment illustrated in FIG. 1.

In a case where the operator manually inserts the catheter, in the slave device 20, the catheter is released from movement control by the detection actuator 204 and the rotation actuator 205, and can be operated in a similar manner to the conventional catheter.

At this time, it is assumed that the catheter is inserted to a position in front of near the lesion by the operator, and the tactile force transmission processing is started with this state as an initial state.

In a case where the tactile force transmission processing is started, the catheter is held for movement control by the detection actuator 204 and the rotation actuator 205, the slave device 20 moves the catheter in accordance with an operation on the master device 10, and external force input to the catheter is fed back from the slave device 20 to the master device 10. At this time, the master device 10 outputs the friction compensation amount being set on the basis of the moving average value of the advancing and retracting velocity of the catheter as a force for assisting the operation of the operator.

In the tactile force transmission processing according to the present modification, as in the first embodiment, the friction compensation amount obtained by multiplying the moving average value (that is, the moving average value) of the advancing and retracting velocity of the catheter in the section defined in the past by the friction compensation coefficient is output as the force for assisting the operation of the user in the master device 10.

In the present modification, since a distance for moving the catheter by the actuator is relatively short, it is sufficient to provide an actuator having a short stroke such as a voice coil motor.

As described above, also in a case where the catheter is inserted into the subject by the control system 1 of the present modification, similarly to the control system 1 of the first embodiment, the friction compensation amount calculated from the moving average value of the advancing and retracting velocity of the catheter in the section defined in the past is output as the force for assisting the operation of the operator in the master device 10.

As a result, it is possible to make it easy to perceive the state change of the slave device 20 while reducing the burden of the user who operates the master device 10, and it is possible to suppress a situation in which a single vibration occurs in the catheter by the force for assisting the operation.

Therefore, the control for friction compensation performed in the master-slave system can be made more appropriate.

Note that, also in the control system 1 of the present modification, similarly to the second embodiment, the friction compensation amount calculated from the moving average value with the forgetting coefficient may be output as a force for assisting the operation of the operator in the master device 10.

Other Modifications

The above-described embodiments and modifications may be appropriately combined and implemented. For example, the control for friction compensation in the first embodiment or the second embodiment and the control for inclination compensation in the first modification can be executed together.

In this case, the force obtained by adding the friction compensation amount in the first embodiment or the second embodiment and the inclination compensation amount in the first modification can be output as the force for assisting the operation in the master device 10.

As a result, it is possible to suppress a situation in which a single vibration is generated in the catheter by the force assisting the master device 10 while suppressing the influence of gravity due to the inclination.

In addition, in the embodiment described above, the description has been made assuming that the force in the thrust direction (advancing and retracting direction) of the catheter is subjected to tactile force transmission between the master device 10 and the slave device 20, but the present invention is not limited thereto. For example, the force related to the rotation about the rotation axis along the advancing and retracting direction or the operation of the end effector may be subjected to the tactile force transmission between the master device 10 and the slave device 20. In this case, the friction compensation amount calculated from the moving average value or the moving average value with the forgetting coefficient of the advancing and retracting velocity of the catheter in the section defined in the past may be output as the force for assisting the operation of the operator in the master device 10.

Furthermore, in the embodiment described above, the case has been described as an example where the actuator included in the master device 10 and the actuator included in the slave device 20 are associated on a one-to-one basis to perform tactile force transmission, but the present invention is not limited thereto. That is, a plurality of actuators of the master device 10 can be associated with one actuator of the slave device 20 to transmit tactile force, or one actuator of the master device 10 can be associated with a plurality of actuators of the slave device 20 to transmit tactile force. Furthermore, a plurality of actuators of the master device 10 can be associated with a plurality of actuators of the slave device 20 to transmit tactile force. As an example, the insertion actuator 203 and the detection actuator 204 of the slave device 20 illustrated in FIG. 3 can be associated with the insertion actuator 103 of the master device 10 to transmit tactile force. In this case, it is not necessary to provide the detection actuator 104 of the master device 10, and cost reduction, weight reduction of the device, and the like can be implemented.

Furthermore, in the embodiment described above, the configuration including the insertion actuator 203 and the detection actuator 204 as the actuators for advancing and retracting the catheter of the slave device 20 has been described as an example, but the present invention is not limited thereto. That is, the catheter of the slave device 20 may be advanced and retracted by one actuator as long as the actuator satisfies the required performance in a stroke and accuracy of an operation.

As described above, the control system 1 according to the present embodiment includes the master device 10, the slave device 20, and the control device 30. Furthermore, the control device 30 includes the friction compensation control unit 352 and the tactile force transmission unit 353.

The friction compensation control unit 352 calculates a force for assisting an operation in the master device 10 with respect to friction generated in the slave device 20 on the basis of a moving average of velocity of a movable portion in the slave device 20.

The tactile force transmission unit 353 assists the operation in the master device 10 with a force calculated by the friction compensation control unit 352 and controls tactile force transmission in the master device 10 and the slave device 20.

As a result, the control for friction compensation performed in the master-slave system can be made more appropriate.

The friction compensation control unit 352 calculates a simple moving average value of the velocity of the movable portion in the slave device 20 in the section defined in the past, and calculates a force for assisting the operation in the master device 10 on the basis of the simple moving average value.

As a result, when compensating for the frictional force being input to the slave device 20, it is possible to suppress a situation in which a single vibration occurs in the catheter by the force for assisting the operation.

The friction compensation control unit 352 calculates a moving average value with a forgetting coefficient obtained by multiplying the moving average value of the velocity of the movable portion in the slave device 20 in a section defined in the past by a forgetting coefficient, and calculates a force for assisting the operation in the master device 10 on the basis of the moving average value with the forgetting coefficient.

As a result, even in a case where an external force is input to the slave device 20 due to a transient noise, the force for assisting the advancing and retracting of the catheter caused by the external force and the elastic force of the catheter are balanced, so that it is possible to suppress the catheter from being temporarily stopped in the middle of vibration, and the like.

Therefore, the control for friction compensation performed in the master-slave system can be made more appropriate.

The friction compensation control unit 352 calculates a force for assisting the operation in the master device 10 with respect to gravity acting on the slave device 20 on the basis of a component of gravity acting in a travel direction of the movable portion in the slave device 20.

The tactile force transmission unit 353 assists an operation in the master device 10 with a force obtained by adding the respective forces calculated by the friction compensation control unit 352 to the friction generated in the slave device 20 and the gravity acting on the slave device 20, and controls tactile force transmission in the master device 10 and the slave device 20.

As a result, it is possible to suppress a situation in which a single vibration is generated in the catheter by the force assisting the master device 10 while suppressing the influence of gravity due to the inclination.

Note that the present invention is not limited to the embodiment described above, and modification, improvement, and the like within a range in which the object of the present invention can be achieved are included in the present invention.

For example, the present invention can be implemented not only as the control system 1 in the embodiment described above, but also as a control device that controls the control system 1, a control method including each step executed in the control system 1, or a program executed by a processor to implement the functions of the control system 1.

Furthermore, in the embodiment described above, the configuration has been described as an example in which the control device 30 is implemented as an independent device, but the functions of the control device 30 can be mounted on one of the control unit 101 of the master device 10 and the control unit 201 of the slave device 20, or can be mounted in a distributed manner on both of them.

Furthermore, the processing in the embodiment described above can be executed by either hardware or software.

That is, it is sufficient that the control system 1 has a function capable of executing the processing described above, and what functional configuration and hardware configuration are used to implement this function is not limited to the examples described above.

In a case where the processing described above is executed by software, a program constituting the software is installed in a computer from a network or a storage medium.

The storage medium storing the program includes a removable medium distributed separately from the device main body, a storage medium incorporated in the device main body in advance, or the like. The removable medium includes, for example, a semiconductor memory, a magnetic disk, an optical disk, a magneto-optical disk, or the like. The optical disk includes, for example, a compact disk-read only memory (CD-ROM), a digital versatile disk (DVD), a Blu-ray Disc (registered trademark), or the like. The magneto-optical disk includes a mini-disk (MD) or the like. Furthermore, the storage medium incorporated in the device main body in advance includes, for example, a read only memory (ROM) or a hard disk in which the program is stored, a semiconductor memory, or the like.

Note that the embodiment described above indicates an example to which the present invention is applied, and does not limit a technical scope of the present invention. That is, the present invention can be subjected to various changes such as omission and replacement without departing from the gist of the present invention, and various embodiments other than the embodiment described above can be taken. Various embodiments and modification thereof that can be taken by the present invention are included in the invention described in the claims and an equivalent scope thereof.

REFERENCE SIGNS LIST

1 Control system
10 Master device
20 Slave device
30 Control device
40 Network
L Display
C Camera
FT Function-specific force/velocity distribution transformation block
FC Ideal force origin block
PC Ideal velocity (position) origin block
IFT Inverse transformation block
S Control object system
101, 201 Control unit
102, 202 Communication unit
103, 203 Insertion actuator
104, 204 Detection actuator
105, 205 Rotation actuator
106, 206 Operation actuator
107, 108, 207, 208 Linear encoder
109, 110, 209, 210 Rotary encoder
111 to 114, 211 to 214 Driver
311 Processor
312 ROM
313 RAM
314 Bus
315 Input unit
316 Output unit
317 Storage unit
318 Communication unit
319 Drive
331 Removable medium
351 Sensor information acquisition unit
352 Friction compensation control unit
353 Tactile force transmission unit
371 Control parameter storage unit

The invention claimed is:

1. A control system including a master device to which an operation by an operator is input and a slave device that operates in accordance with the operation input to the master device, the control system comprising:

a control amount calculation means that calculates a force for assisting an operation in the master device based on information relating to moving of a movable portion in the slave device;

a control means that assists the operation in the master device with the force calculated by the control amount calculation means and control tactile force transmission in the master device and the slave device; and wherein the control amount calculation means calculates the force for assisting the operation in the master device with respect to friction generated in the slave device based on a moving average of velocity of the movable portion in the slave device.

2. The control system according to claim 1, wherein the control amount calculation means calculates a simple moving average value of the velocity of the movable portion in the slave device in a section defined in the past, and calculates a force for assisting the operation in the master device based on the simple moving average value.

3. The control system according to claim 1, wherein the control amount calculation means calculates a moving average value with a forgetting coefficient obtained by multiplying the moving average value of the velocity of the movable portion in the slave device in a section defined in the past by a forgetting coefficient, and calculates a force for assisting the operation in the master device based on the moving average value with the forgetting coefficient.

4. The control system according to claim 1, wherein the control amount calculation means calculates a force for assisting the operation in the master device with respect to gravity acting on the slave device based on a component of gravity acting in a travel direction of the movable portion in the slave device, and the control means assists the operation in the master device with a force obtained by adding each force calculated by the control amount calculation means to friction generated in the slave device and gravity acting on the slave device, and controls tactile force transmission in the master device and the slave device.

5. The control system according to claim 1, wherein the control amount calculation means calculates the force for assisting an operation in the master device based on a component of gravity acting in a travel direction of the movable portion in the slave device.

6. A control device that controls tactile force transmission in a master device to which an operation by an operator is input and a slave device that operates in accordance with the operation input to the master device, the control device comprising:

a control amount calculation means that calculates a force for assisting an operation in the master device based on information relating to moving of a movable portion in the slave device;

a control means that assists the operation in the master device with the force calculated by the control amount calculation means and control tactile force transmission in the master device and the slave device; and wherein the control amount calculation means calculates the force for assisting the operation in the master device with respect to friction generated in the slave device based on a moving average of velocity of the movable portion in the slave device.

7. A control method executed by an information presentation system including a master device to which an operation by an operator is input and a slave device that operates in accordance with the operation input to the master device, the control method comprising:

a control amount calculation step of calculating a force for assisting an operation in the master device based on information relating to moving of a movable portion in the slave device;

a control step of assisting the operation in the master device with the force calculated in the control amount calculation step and controlling tactile force transmission in the master device and the slave device; and wherein the control amount calculation step calculates the force for assisting the operation in the master device with respect to friction generated in the slave device based on a moving average of velocity of the movable portion in the slave device.

* * * * *